United States Patent
Bengs et al.

(12) 
(10) Patent No.: US 6,746,665 B1
(45) Date of Patent: Jun. 8, 2004

(54) SUN PROTECTION PRODUCT WITH MICROPARTICLES ON THE BASIS OF WATER-INSOLUBLE LINEAR POLYGLUCAN

(75) Inventors: Holger Bengs, Frankfurt (DE); Alfred Braunagel, Mainz (DE)

(73) Assignee: Celanese Ventures GmbH (DE)

( * ) Notice: Subject to any disclaimer, the term of this patent is extended or adjusted under 35 U.S.C. 154(b) by 0 days.

(21) Appl. No.: 09/869,394

(22) PCT Filed: Nov. 30, 1999

(86) PCT No.: PCT/EP99/09291

§ 371 (c)(1),
(2), (4) Date: Feb. 25, 2002

(87) PCT Pub. No.: WO00/38622

PCT Pub. Date: Jul. 6, 2000

(30) Foreign Application Priority Data

Dec. 28, 1998 (DE) ......................... 198 60 368

(51) Int. Cl.⁷ ............................. A61K 7/42; A61K 7/44; A61K 7/00
(52) U.S. Cl. ............................. 424/59; 424/60; 424/400; 424/401
(58) Field of Search ............................... 424/400, 401, 424/59, 60

(56) References Cited

U.S. PATENT DOCUMENTS

| 5,486,507 A | 1/1996 | Whistler |
| 6,548,075 B1 * | 4/2003 | Bengs et al. ............ 424/401 |

FOREIGN PATENT DOCUMENTS

| DE | 19827978 A1 | 12/1999 |
| DE | 198 39 216 | 1/2000 |
| EP | 0487000 B1 | 8/1995 |
| GB | 2 247 242 | 2/1992 |
| JP | 11246379 | 9/1999 |
| WO | WO 94 18932 | 1/1994 |
| WO | WO 97 28780 | 8/1997 |
| WO | WO 9911695 | 3/1999 |

OTHER PUBLICATIONS

Schrader et al. "Unusual Features in the Development and Testing of Sun Protection Formulations Containing Micropigments", SOFW Journal, 124, pp. 478–487, 8/98.

Eggensperger et al. "Multiactive Polysaccharides Part I–Fungus Extracts and Part II– Vegetable Polysaccharides", SOFW Journal, 123, pp. 542–546, 8/97 and pp. 838–842, 12/97.

Pauly et al. "New Polysaccharides Interest in Care Cosmetology" IN–COSMETICS 1997, Conference proceedings, pp. 417–444.

Search Report of Feb. 15, 2000.

Inaba, R. et al: "Application of Porous Starch Complex Powder" J. SCCJ (1995) 29(2) 146–53; Abstract.

* cited by examiner

*Primary Examiner*—Shelley A. Dodson
(74) *Attorney, Agent, or Firm*—Gilberto M. Villacorta; Serge Sira; Katten Muchin Zavis Rosenman

(57) ABSTRACT

The present invention relates to a sun protection product which contains microparticles as the active agent, wherein the microparticles comprise water-insoluble linear polyglucan.

20 Claims, No Drawings

SUN PROTECTION PRODUCT WITH MICROPARTICLES ON THE BASIS OF WATER-INSOLUBLE LINEAR POLYGLUCAN

DESCRIPTION

The present invention relates to a sun protection product with microparticles on the basis of water-insoluble linear polyglucan which, on the one hand, ensures good UV protection and appears transparent upon application.

Known sun protection products comprise inter alia pigments, such as, for example, titanium dioxide and zinc oxide as such or in the form of "micronized particles" as light protection filters. From a cosmetics viewpoint, these pigments have the disadvantage that they whiten, i.e. make the skin appear white in colour.

As a compromise for reducing the whitening to a tolerable degree and nevertheless achieving an acceptable UV protection, these pigments are usually used with a comparatively small particle size between 10 and 100 nm (A. Schrader, M. Rohr "Auffälligkeiten bei der Entwicklung und Prufung von mikropigmenthaltigen Sonnenschutzformulierungen [Unusual features in the development and testing of sun protection formulations containing micropigments]" SÖW Journal, 124, pages 478–487, 8/98).

In addition, titanium dioxide is to be viewed critically from a health viewpoint. In a study using titanium dioxide which had been extracted from sun protection products, it was observed upon irradiation with sunlight that titanium dioxide is able to catalyze photooxidation and damages bacterial DNA (CTFA/TRN Volume 12, No. 3, page 5 (1998) with reference to FEBS Letters, 418, 87–90, 1997).

A light-protecting action is also known for individual polysaccharides. For example, a light-protecting action has been described for poly-$\beta$-1,3-glucans (H. Eggensperger, M. Wilker, "Multiaktiv wirksame Polysaccharide Teil I-Pilzextrakte und Teil II-Pflanzliche Polysaccharide [Multiactive polysaccharides part I-fungus extracts and part II-vegetable polysaccharides]" in SÖW Journal, 123, 8/97, pages 542–546 and 12/97, pages 838–842).

Poly-$\beta$-1,3-glucans which can be obtained from yeasts have a linear structure with a small proportion of $\beta$-1,6 branching.

It has also been proposed to use glycogen (a highly branched poly-1,4-$\alpha$-glucan with branching in the 6-position) obtained biotechnologically or from marine molluscs for sun protection products (M. Pauly, G. Pauly "New Polysaccharides Interest in Care Cosmetology" IN-COSMETICS 1997, Conference Proceedings, pages 417–444, Verlag für chemische Industrie, H. Ziolkowsky GmbH, 1998).

EP-B-0 487 000 proposes the use of a cosmetic composition in the form of an emulsion having 15 to 40% by weight of an enzymatically debranched starch in sun protection products, where the enzymatically degraded starch is a linear poly-1,4-$\alpha$-glucan having 15 to 65 anhydroglucose units. However, there is no reference to a potential light protection action of the enzymatically debranched starch used therein; instead, it is used as an emulsifying auxiliary.

In view of the risks of intensive UV exposure, there is a growing need for suitable sun protection filters which not only offer reliable protection, but also do not impair the external appearance and are thus also suitable for daily use.

According to the invention, this object is achieved by a sun protection product which comprises, as effective constituent, spherical microparticles which consist entirely or partially of at least one water-insoluble linear polyglucan.

The novel sun protection products with spherical microparticles which consist entirely or partially of at least one water-insoluble linear polyglucan can ensure excellent UV protection and in addition the microparticles appear transparent, even in high concentrations.

Moreover, the microparticles used according to the invention form stable suspensions or dispersions even without the addition of dispersion auxiliaries. This is advantageous in particular for the use in emulsion-based sun protection products since the addition of dispersion auxiliaries can be dispensed with or the amount thereof can be reduced, thus simplifying and reducing the cost of production.

In addition, the spherical microparticles convey a pleasant soft feel upon application, which is attributed to their regular structure.

For the sun protection products according to the invention, recourse may be had to the formulations and additives customary for such products. Particularly preferred bases for formulations are emulsions, such as, for example, O/W or W/O emulsions, aqueous or fat-containing gels, hydrogels, oils, emulsifier-free formulations, etc. The sun protection products can be used in the form of creams, lotions, sprays, fluids, powders, etc.

Apart from the microparticles, the sun protection products according to the invention can also comprise further known UV filters.

The proportion of the microparticles in the sun protection products according to the invention is governed by the base used. It may be up to 70% by weight, based on the total weight of the sun protection product, e.g. in wax-oil bases as are used inter alia for "sun protection cream compacts". In general, amounts of from approximately 0.5 to about 20% by weight, preferably about 2 to about 15% by weight and in particular about 3 to about 10% by weight, suffice. An amount less than 0.5% by weight is of no importance for UV protection.

It goes without saying that the amount depends heavily on the composition of the product. If the sun protection product comprises further UV filters or if the base of the sun protection product is itself colored or pigmented, such as, for example, pigmented W/O or O/W emulsions, such that UV permeability is reduced from the outset, it is possible for smaller amounts of microparticles to be sufficient. For UV-permeable bases, e.g. transparent bases, such as, for example, unpigmented emulsions, oils or gels, it is advantageous to add larger amounts of microparticles.

The required amount can, however, be determined directly from case to case by a person skilled in the art with a few routine experiments.

The microparticles used for the sun protection products according to the invention can have an average diameter Dn (number-average) of 1 nm–100 $\mu$m, preferably 50 nm–10 $\mu$m, in particular 100 nm–3 $\mu$m and particularly preferably less than 1 $\mu$m, in particular less than 0.2 $\mu$m.

For the present invention, spherical microparticles are to be understood as meaning microparticles which have a virtually spherical shape. If a sphere is described by axes of identical length which start from a common origin and are directed into space and define the radius of the sphere in all spatial directions, the lengths of the axes may deviate from an ideal spherical state by from 1% to 40% for the spherical particles. The deviation is preferably 25% or less, particularly preferably 15% or less.

The spherical particles have a regular surface which can be compared macroscopically with a raspberry, where the depth of irregularities on the particle surface, such as recesses or indentations, is at most 20%, preferably 10%, of the average diameter of the spherical microparticles.

The specific surface area of the microparticles is generally from 1 m²/g to 100 m²/g, preferably 1.5 m²/g to 20 m²/g and particularly preferably 3 m²/g to 10 m²/g. Furthermore, the particles according to the invention preferably have a dispersity D=weight-average diameter ($d_w$)/number-average diameter ($d_n$) of from 1.0 to 10.0, in particular from 1.5 to 5.0 and particularly preferably from 2.0 to 3.0.

The averages used herein are defined as follows:

$d_n$=sum of $n_i \times d_i$/sum of $n_i$=number-average $d_w$=sum of $n_i \times d_i^2$/sum of $n_i \times d_i$=weight-average $n_i$=number of particles with diameter $d_i$, $d_i$=a particular diameter, i=serial parameter.

In this connection, the term weight indicates a weighted average, as a result of which the larger diameters are given greater importance.

The microparticles used according to the invention may also have been subjected to a surface modification by, for example, derivatizing functional groups, such as hydroxyl groups, of the polyglucans.

For the purposes of the present invention, linear water-insoluble polyglucans are polysaccharides built up from glucans as monomeric building blocks such that the individual building blocks are always linked together in the same way. Each basic unit or building block defined in this way has exactly two linkages, each to one other monomer. The only exceptions to this are the two base units which form the start and the end of the polysaccharide. These have only one linkage to a further monomer and form the end-groups of the linear polyglucan.

If the base unit has three or more linkages, then this is referred to as branching. In this context, the number of hydroxyl groups per 100 base units which are not involved in constructing the linear polymer backbone and form the branches gives the "degree of branching". According to the invention, the linear water-insoluble polyglucans have a degree of branching of at most 8%, i.e. they have a maximum of 8 branches and 100 base units. The degree of branching is preferably less than 4% and in particular at most 2.5%.

Particular preference is given to polyglucans whose degree of branching in the 6-position is less than 4%, preferably at most 2% and in particular at most 0.5, and is preferably in each case at most 2% and in particular 1% in the other positions, e.g. in the 2- or 3-position. Particular preference is also given to polyglucans with a degree of branching in the 6-position of less than 0.5.

Of particular suitability for the invention are polyglucans which have no branches or whose degree of branching is so minimal that it is no longer detectable by traditional methods.

Examples of preferred water-insoluble linear polyglucans are linear poly-D-glucans, the nature of the linkage being unimportant, provided there is linearity within the meaning of the invention. Examples are poly-alpha-D-glucans, in particular poly-1,4-alpha-D-glucan, and poly-1,3-beta-D-glucans, particular preference being given to poly-1,4-α-D-glucan.

For the present invention, the prefixes "alpha", "beta" or "D" refer solely to the linkages forming the polymer backbone and not to the branches.

For the present invention, the term "water-insoluble polyglucan" is to be understood as meaning compounds which, according to the definition of the German Pharmacopoeia (DAB=Deutsches Arzneimittelbuch, Wissenschaftliche Verlagsgesellschaft mbH, Stuttgart, Govi-Verlag, Frankfurt, [lacuna] edition, 1987), fall into the categories "slightly soluble", "sparingly soluble", "very sparingly soluble" and "virtually insoluble" compounds, corresponding to classes 4 to 7.

In the case of the polyglucans used according to the invention, this means that at least 98% of the amount used, in particular at least 99.5%, are insoluble in water under standard conditions (T=25° C.+/−20%, p=101325 Pascal+/−20%) (corresponding to classes 4 and 5, respectively).

For the present invention, preference is given to sparingly soluble to virtually insoluble compounds, in particular very sparingly soluble to virtually insoluble compounds.

"Very sparingly soluble" corresponding to class 6 can be illustrated by the following protocol:

One gram of the polyglucan to be investigated is heated in 1 l of deionized water to 130° C. at a pressure of 1 bar. The solution which forms only remains stable briefly for a few minutes. Upon cooling under standard conditions, the substance precipitates out again. After cooling to room temperature and separation by means of centrifugation, at least 66% of the amount used can be recovered, taking into account experimental losses.

The polyglucans used according to the invention may be of any origin provided the conditions given above with regard to the terms "linear" and "water-insoluble" are met.

They may have been obtained naturally or by biotechnology methods.

For example, they may be obtained from natural vegetable or animal sources by isolation and/or purification. It is also possible to use sources which have been manipulated genetically such that they contain a higher proportion of unbranched or comparatively slightly branched polyglucans than the unmanipulated source.

They may have been prepared from non-linear polyglucans by enzymatic or chemical debranching. In this connection, non-linear polyglucans which contain branches may be treated with an enzyme such that cleavage of the branches arises, leaving, following removal of the branches, linear polyglucans. These enzymes may, for example, be amylases, isoamylases, gluconohydrolases, pullulanases or cyclomaltodextrin glucanotransferases.

Biotechnology methods include biocatalytic, including biotransformation, or fermentation processes.

Linear polyglucans prepared by biocatalysis (including: biotransformation) for the purposes of this invention means that the linear polyglucan is prepared by catalytic reaction of monomeric basic building blocks such as oligomeric saccharides, e.g. of monosaccharides and/or disaccharides, using a biocatalyst, usually an enzyme, under suitable conditions. In this connection, reference is also made to "in vitro biocatalysis".

Linear polyglucans from fermentations are, within the language usage of the invention, linear polyglucans which are obtained by fermentation processes using naturally occurring organisms, such as fungi, algae, bacilli, bacteria or protists or using non-naturally occurring organisms, but using natural organisms modified by genetic methods of the general definition, such as fungi, algae, bacilli, bacteria or protists, or which can be obtained with the insertion and assistance of fermentation processes. Reference is also made in this connection to "in vivo biocatalysis".

Examples of such microorganisms are Pichiapastoris, Trichoderma reseii, Staphyloccus carnosus, Escherichia coli, Aspergillus niger.

Advantageous processes for the biotechnology production are described, for example, in WO 95/31553 or the previously unpublished German patent application from the applicant with the official file reference 198 27 978.5.

According to WO 95/31553, amylosucrases are used for the preparation of linear water-insoluble polyglucans, such as poly-1,4-α-D-glucan, by means of a biocatalytic process. Further suitable enzymes are polysaccharide synthases, starch synthases, glycol transferases, 1,4-α-D-glucan transferases, glycogen synthases or phosphorylases.

It is also possible to use modified water-insoluble linear polyglucans, it being possible for the polyglucans to have been chemically modified, for example by esterification and/or etherification in one or more positions which are not involved in the linear linkage. In the case of the preferred 1,4 linked polyglucans, the modification can take place in the 2-, 3- and/or 6-position.

For the purposes of the invention, modification means that the hydroxyl groups present which are not involved in the linkage are chemically changed. This excludes a ring opening of the glucan units, as occurs, for example, during oxidative carboxylation or hydrolysis. Measures for such modifications are sufficiently known to the person skilled in the art.

Thus, linear polyglucans, such as, for example, pullulans, which are per se water-soluble, can be made water-insoluble by modification.

For the present invention, use is preferably made of water-insoluble linear polyglucans which have been prepared in a biotechnology process, in particular in a biocatalytic or a fermentation process.

In contrast to polyglucans which are isolated from natural sources, such as plants, the linear water-insoluble polyglucans obtained here have a particularly homogeneous property profile, e.g. with regard to the molecular weight distribution, they contain no, or at worst only very small amounts, of undesired byproducts, which have to be separated off at great expense or could trigger allergic reactions, and can be reproduced in a precisely specified manner in a simple way.

In particular, biotechnology methods may be used to obtain water-insoluble linear polyglucans, such as, for example, the preferred poly-1,4-α-D-glucans which do not contain branches or whose degree of branching is below the detection limit of traditional analytical methods.

In addition, the polyglucans can be used in the form of "alpha-amylase-resistant polyglucans", as are described using the example of poly-1,4-α-D-glucan in the previously unpublished German patent application with an earlier priority date and having the official file reference 198 30 618.0 from the applicant.

Alpha-amylase-resistant polyglucans can be obtained by preparing a suspension or dispersion of water-insoluble polyglucans and water, heating the suspension or dispersion to a temperature in the range from 50 to 100° C., allowing the resulting paste-like mixture to cool to a temperature in the range from 50° C. down to the freezing point, preferably 35 to 15° C., 27 to 22° C., 16 to 0° C. or 6 to 2° C., over a period of from 1 to 72 h, preferably 1 to 36 h and in particular 15 to 30 h and retrograding the paste-like mixture at a temperature, lower than the temperature of the heated paste-like mixture in a temperature range from 90 to 4° C., and, if desired, drying or dewatering the resulting product.

The polyglucan can also be used as thermoplastic polyglucan obtainable by melting on linear water-insoluble polyglucan and adding at least 20% by weight, preferably at least 30% by weight, of a softener such as sorbitol, glycerol, condensation products thereof and oligomers, DMSO, succinic acid, citric acid monohydrate, malic acid, tartaric acid, etc. at about 170° C.

A description of suitable measures and properties of thermoplastic polyglucans using the example of the preferred linear water-insoluble poly-1,4-α-D-glucan is given in the previously unpublished German patent application which has an earlier priority date and the office file reference 198 52 826, to which express reference is made here.

The molecular weights $M_w$ (weight-average, determined by means of gel permeation chromatography relative to calibration with a pullulan standard) of the linear polyglucans used according to the invention can vary within a wide range from $0.75 \times 10^2$ g/mol to $10^7$ g/mol. The molecular weight $M_w$ is preferably in a range from $10^3$ g/mol to $10^6$ g/mol and particularly preferably from $10^3$ g/mol to $10^5$ g/mol. A further advantageous range is from $2 \times 10^3$ to $8 \times 10^3$. Corresponding ranges apply to the preferably used poly-1,4-D-glucan.

The molecular weight distribution or polydispersity $M_w/M_n$ may likewise vary within wide ranges depending on the polyglucan preparation process. Preferred values are from 1.01 to 50, in particular from 1.01 to 15. Particular preference is given to polyglucans with low dispersity values, such as e.g. 1.01–2.5. The polydispersity increases with a bimodal distribution of the molecular weights.

For the preparation of the microparticles it is possible to use a single polyglucan, in particular poly-1,4-D-glucan and very particularly poly-1,4-α-D-glucan or mixtures of two or more representatives.

In a further embodiment, a water-insoluble branched polysaccharide, preferably a polyglucan, in particular a poly-1,4-alpha-D-glucan or a poly-1,3-beta-D-glucan, can be added. It is also possible to add mixtures of two or more branched polysaccharides.

The branched polysaccharides can be of any origin. In this connection, reference is made to the explanations regarding this for the linear water-insoluble polyglucans. Preferred sources are starch and starch analogs, such as glycogen. If required, the proportion of linear structures in the branched polysaccharides can be increased by suitable enrichment methods.

For the insolubility in water, the same data apply as for the linear water-insoluble polyglucan, the molecular weight can also be higher for the branched polysaccharides, e.g. values up to, preferably, $10^9$ g/mol and above.

It is also possible to admix other polymers, in particular biocompatible or biodegradable polymers. Here, the amount of the other polymer(s) which is/are admixed, without the spherical shape and/or other properties of the microparticles to be prepared being changed, is always dependent on the polymer added.

To ensure the desired properties of the microparticles, the proportion of linear water-insoluble polyglucan should be at least 70% by weight, in particular 80% by weight and preferably 90% by weight, based on the total content of linear water-insoluble polyglucan including optionally branched polysaccharide and optionally, further polymers.

According to a particularly preferred embodiment, the microparticles consist to an extent of 100% by weight of linear water-insoluble polyglucan, in particular linear water-insoluble poly-1,4-α-D-glucan which has preferably been obtained biocatalytically.

Examples of processes for the preparation of the microparticles are, for example, precipitation processes or spray-drying processes.

The spherical microparticles can be prepared by dissolving the water-insoluble linear polyglucan or a mixture of two or more thereof and optionally further polymers in a solvent, e.g. DMSO, introducing the solution into a precipitating agent, e.g. water, preferably at a temperature of from 20° C. to 60° C., if required cooling the solution to a temperature of from −10° C. to +10° C. and separating off the particles formed in the process.

Here, the dissolution operation of the polyglucan used as starting material can be carried out at room temperature or at higher temperatures. The concentration of linear water-insoluble polyglucan including optionally branched polysaccharide and further polymers in the solvent can vary within wide limits according to requirement. Preferably, it is in a range from 0.02 g/ml to 1.0 g/ml, in particular from 0.05 g/ml to 0.8 g/ml and particularly preferably from 0.3 g/ml to 0.6 g/ml.

Examples of precipitating agents are water, dichloromethane, a mixture of water and dichloromethane, and mixtures of water and alcohols such as methanol, ethanol, isopropanol, particular, preference being given to water and to a mixture of water and dichloromethane.

The ratio of solvent to precipitating agent is preferably chosen in a range from 1:1000 to 1:4 (part of solvent/parts of precipitating agent), preferably 1:100 to 1:10 and in particular 1:70 to 1:30.

It is generally unimportant here in which order the solvent and the precipitating agent are combined, e.g. whether the precipitating agent is added to the solvent or vice versa. However, it is important that rapid thorough mixing is ensured.

The precipitating process can be carried out relatively slowly at low temperature overnight.

It can be influenced and controlled by varying the temperature and the precipitating agent. If cooling is carried out, it must be ensured that the mixture of solvent and precipitating agent remains liquid and does not solidify.

By co-using suitable additives, it is possible to influence the properties of the microparticles, such as size, surface structure, porosity, etc. and the way in which the process is carried out.

Suitable additives are, for example, surface-active substances, such as sodium dodecyl sulfate, N-methylgluconamide, polysorbates (e.g. Tween (registered trademark)), alkylpolyglycol ethers, ethylene oxide-propylene oxide block polymers (e.g. Pluronic (registered trademark)), alkylpolyglycol ether sulfates, generally alkyl sulfates and fatty acid glycol esters, and sugars, such as, for example, fructose, sucrose, glucose, water-soluble cellulose or hot-water-soluble poly-alpha-D-glucan, such as, for example, natural or chemically modified starches, poly-alpha-D-glucans obtained from these starches, and starch-analogous compounds.

These additives are usually added to the precipitating agent. The amount used depends on the individual case in question and the desired particle properties, the determination of the advantageous amount in each case being known to the person skilled in the art.

By adding water-soluble cellulose derivatives to the precipitating agent, it is possible to obtain microparticles having a particularly smooth surface, the depth of the irregularities on the surface of the microparticles generally being at most 10% of the average diameter. Examples of water-soluble cellulose derivatives are cellulose esters and cellulose ethers, mixed forms thereof, such as, for example, hydroxypropylmethylcelluloses, hydroxyethylcelluloses, carboxymethylcelluloses, cellulose acetates, cellulose butyrates, cellulose propionates, cellulose acetobutyrates, cellulose acetopropionates, cellulose nitrates, ethylcelluloses, benzylcelluloses, methylcelluloses, etc. It is also possible to use mixtures of different water-soluble cellulose derivatives.

For the present invention, the term "water-soluble cellulose derivatives" is understood as meaning compounds which, according to the definition of the German Pharmacopoeia (DAB=Deutsches Arzneimittelbuch, Wissenschaftliche Verlagsgesellschaft mbH, Stuttgart, Govi-Verlag GmbH, Frankfurt, 9th edition, 1987), fall into the category very readily soluble to sparingly soluble.

The concentration of the water-soluble cellulose derivative in the precipitating agent is of no further importance. The upper limit automatically arises from the resulting viscosity and thus the processability of the resulting solution.

Concentrations of from 2 g (cellulose derivative)/l (precipitating agent) to 150 g/l, preferably from 5 g/l to 80 g/l and in particular 8 g/l to 20 g/l, have proven advantageous.

The proportion of particularly small particles having an average diameter of from 1 nm to 2 $\mu$m can be increased by adding hot-water-soluble poly-alpha-D-glucan to the precipitating agent.

For this purpose, it is possible to use the same poly-alpha-D-glucan compounds as have been mentioned in connection with the linear water-insoluble polyglucan, provided they satisfy the feature of being hot-water-soluble.

Preferred examples are natural or chemically modified starches, poly-alpha-D-glucans obtained from these starches, and starch-analogous compounds.

Starch-analogous compounds are understood as meaning compounds which consist of poly-alpha-D-glucans, but are nonvegetable in origin. One example thereof is glycogen or dextran. The hot-water-soluble poly-alpha-D-glucans can be used as a mixture of a linear fraction and a branched fraction, as is present, for example, in starch. In this case, the proportion of linear poly-alpha-D-glucan should be more than 15% by weight, preferably 50 to 99.5% by weight, in particular 60 to 90% by weight and very particularly preferably 65 to 80% by weight, based on the total amount of poly-alpha-D-glucan in the precipitating agent.

They may, however, also consist of branched structures, as are present, for example, in amylopectin or in glycogen.

For the purposes of the present invention, "hot-water-soluble" means that the poly-alpha-D-glucans are essentially insoluble at room temperature, the same criterion preferably applying as for the term "water-insoluble" in connection with linear polysaccharides. The term "solution" or "solubility" are in particular also understood as meaning suspensions and the formation of suspensions, respectively, as arise in the case of the dissolution of starch.

For example, the hot-water-soluble starches preferred according to the invention exhibit virtually no solubility in water at room temperature, while the "cold-water-soluble" starches are more readily soluble under these conditions.

The hot-water-soluble starches are characterized in particular by the fact that, upon heating under autogenous pressure, e.g. in an autoclave, to a temperature in the range from about 100 to about 160° C., they form solutions, the temperature in each case depending on the type of starch.

For example, potato starch can be boiled at about 100° C. until dissolution is complete, while corn starch requires a temperature of about 125° C.

For the process according to the invention, the hot-water-soluble poly-alpha-D-glucans are preferably added to the precipitating agent in maximum concentration, i.e. a saturated solution is prepared. Further suitable ranges are from more than 0.001% by weight to 10% by weight, preferably from 0.01 to 2% by weight and in particular from 0.05% by weight to 0.5% by weight, based on the amount of precipitating agent used.

In the case of thermoplastic polyglucan, the additives may be incorporated into the thermoplastic mixture in an advantageous manner as a plasticizer or in addition to the plasticizers, such that a dry powder mixture is present which can then be processed to the microparticles, it also being possible for the formation process of the microparticles to be carried out in the final formulation with incorporation of the thermoplastic polyglucans.

A detailed description of the microparticles used here, their preparation and the water-insoluble linear polyglucans which can be used therefor is given in the German patent applications of the applicant which are previously unpublished but which have an earlier priority date and the file references 197 37 481.6, 198 03 415.6, 198 16 070.4, 198 30 618.0, 198 27 978.7, 198 39 214.1, 198 39 216.8 and 198 39 212.5, to which reference is made for the present description. The three last-named applications relate in particular to processes for the modification of the particle nature, such as surface roughness and size.

In addition, the microparticles used according to the invention are characterized by high biocompatibility. For the biocompatibility of the microparticles used according to the invention, the nature-identical character of the water-insoluble linear polyglucans, and of their degradation products, used for the preparation, in particular, is of great importance.

The present invention is illustrated below by reference to individual examples.

EXAMPLE 1

Preparation of poly(1,4-α-D-glucan) microparticles 500 mg of poly(1,4-α-D-glucan) are dissolved in 2.5 ml of dimethyl sulfoxide (DMSO, analytical grade, from Riedel-de-Haen) at about 70° C. The DMSO solution is added dropwise to 100 ml of double-distilled water with stirring, and the solution is stored overnight at 5° C. The fine milky suspension is centrifuged for 15 minutes at 3500 revolutions per minute, and the supernatant is decanted off. The sediment is slurried with double-distilled water and centrifuged again. The operation is repeated two more times. The suspension is then freeze-dried. 311 mg of white poly(1,4-α-D-glucan) particles are obtained. This corresponds to a yield of 62% of colorless microparticles.

EXAMPLE 2

Assessment of a sun protection product comprising microparticles as in Example 1

The assessment was carried out in accordance with the procedures of the COLIPA sun protection factor test method For the investigation, test persons were chosen who, in the distribution of their UV sensitivity, corresponded to the user majority, those acclimatized to UV were excluded.

Use was made of standard preparations P1 and P3 (Beiersdorf AG) compared with a preparation comprising 5% by weight of microparticles as in Example 1. The essential investigation parameters were:

Use of a Schrader sun simulator (SU 2000, manufacturer PTI-Photon Technology GmbH) which, with a 300 Watt xenon short-arc lamp, produces a light with a representative spectrum which was normalized to the intensity values of 320 nm. The light beam from this lamp was directed using movable mirrors onto six points arranged in the shape of a cross such that the homogeneous irradiation with 6 different light dosages was possible within one sitting. To exactly apply the amount of the light protection product required by the COLIPA standard of 2.0+/−0.04 mg/cm$^2$, the light protection product was applied using a plastic syringe to a plastic spatula and was uniformly distributed using this spatula to the area to be irradiated.

The irradiation fields were read after 20 hours+/−4 hours.

The average sun protection factor (SPF) was calculated according to the following formula, where MED stands for minimum erythemal dose:

$$SPF\ (COLIPA) = MED\ (test\ field)/MED\ (empty\ field)$$

The average sun protection factor was 6.15 with a standard deviation of 0.65. The confidence interval (CI95%) was within 20% of the average.

What is claimed is:

1. A sun protection product which comprises spherical microparticles wherein the spherical microparticles comprise at least one water-insoluble linear polyglucan having a degree of branching of less than 0.5% in the 6-position.

2. The sun protection product as claimed in claim 1, wherein the water-insoluble linear polyglucan has a degree of branching of at most 2% in the other positions.

3. The sun protection product as claimed in claim 1, wherein the microparticles have an average diameter of from 1 nm to 100 μm.

4. The sun protection product as claimed in claim 1, wherein the depth of irregularities on the surface of the microparticles is at most 20% of the average diameter of the microparticles.

5. The sun protection product as claimed in claim 1, wherein the microparticles are present in the sun protection product in an amount of from 05.% to 70% by weight, based on the total weight of the sun protection product.

6. The sun protection product as claimed in claim 1, wherein the water-insoluble linear polyglucan is selected from the group consisting of poly-1,4-□-D-glucan, poly-1,3-□-D-glucan, and or a mixture thereof.

7. The sun protection product as claimed in claim 1, wherein the water-insoluble linear polyglucan is produced by a biotechnological method.

8. The sun protection product as claimed in claim 1, wherein the water-insoluble linear polyglucan is produced biocatalytically.

9. The sun protection product as claimed in claim 1, wherein the microparticles further comprise branched polysaccharides and further polymers.

10. The sun protection product as claimed in claim 1, wherein the microparticles comprise at least 70% water-insoluble linear polyglucan based on the total content of polyglucan in the microparticles.

11. The sun protection product as claims in claim 1, wherein the microparticles comprise 100% of the at least one water-insoluble linear polyglucan.

12. The sun protection product as claimed in claim 1, wherein the microparticles are dispersed in the sun protection product and have a dispersity in the range of from 1.0 to 10.0.

13. A method of making a sun protection product comprising preparing spherical microparticles comprising at least one water-insoluble polyglucan having a degree of branching of less than 0.5% in the 6-position.

14. The method as claimed in claim 13, wherein the microparticles have an average diameter of from 1 nm to 100 μm.

15. The method as claimed in claim 13, wherein the microparticles are dispersed in the sun protection product and have a dispersity in the range of from 1.0 to 10.0.

16. The method as claimed in claim 13, wherein the water-insoluble linear polyglucan is selected from the group consisting of poly-1,4-□-D-glucan, poly-1,3-□-D-glucan, or a mixture thereof.

17. method of sun protection comprising applying a sun protection product which comprises spherical microparticles wherein the spherical microparticles comprise at least one water-insoluble linear polyglucan having a degree of branching of less than 0.5% in the 6-position.

18. The method as claimed in claim 17, wherein the microparticles have an average diameter of from 1 nm to 100 μm.

19. The method as claimed in claim 17, wherein the microparticles are sun protection product and have a dispersity in the range of from 1.0 to 10.0.

20. The method as claimed in claim 17, wherein the water-insoluble linear polyglucan is selected from the group consisting of poly-1,4-□-D-glucan, poly-1,3-□-D-glucan, or a mixture thereof.

* * * * *